US008428710B2

(12) United States Patent
Kuriyama et al.

(10) Patent No.: US 8,428,710 B2
(45) Date of Patent: Apr. 23, 2013

(54) ENDOSCOPIC THERAPEUTIC DEVICE AND DOUBLE TUBE FOR THERAPEUTIC DEVICE (75) Inventors: Saori Kuriyama, Tokyo (JP); Satoru Tomiya, Inagi (JP)

(73) Assignee: Olympus Corporation (JP)

( * ) Notice: Subject to any disclaimer, the term of this patent is extended or adjusted under 35 U.S.C. 154(b) by 716 days.

(21) Appl. No.: 12/104,024

(22) Filed: Apr. 16, 2008

(65) Prior Publication Data
US 2008/0208127 A1 Aug. 28, 2008

Related U.S. Application Data (63) Continuation of application No. PCT/JP2006/320781, filed on Oct. 18, 2006.

(30) Foreign Application Priority Data

Oct. 18, 2005 (JP) ................................. 2005-303202

(51) Int. Cl.
*A61N 1/30* (2006.01)
(52) U.S. Cl.
USPC ........................................................... 604/21
(58) Field of Classification Search .................. 604/29, 604/21, 41
See application file for complete search history.

(56) References Cited

U.S. PATENT DOCUMENTS

| 5,601,588 | A | * | 2/1997 | Tonomura et al. | 606/185 |
| 5,820,546 | A | * | 10/1998 | Ouchi | 600/123 |
| 5,882,293 | A | * | 3/1999 | Ouchi | 600/104 |
| 5,899,850 | A | * | 5/1999 | Ouchi | 600/104 |
| 5,964,740 | A | * | 10/1999 | Ouchi | 604/264 |
| 6,203,533 | B1 | * | 3/2001 | Ouchi | 604/264 |
| 6,210,377 | B1 | * | 4/2001 | Ouchi | 604/264 |
| 6,210,378 | B1 | * | 4/2001 | Ouchi | 604/264 |
| 6,511,462 | B1 | * | 1/2003 | Itou et al. | 604/264 |
| 6,758,806 | B2 | * | 7/2004 | Kamrava et al. | 600/153 |
| 6,929,623 | B2 | * | 8/2005 | Stone | 604/164.01 |

FOREIGN PATENT DOCUMENTS

| JP | 8-336591 | 12/1996 |
| JP | 9-38202 | 2/1997 |
| JP | 2001-58006 | 3/2001 |
| JP | 2004-290367 | 10/2004 |

OTHER PUBLICATIONS

International Search Report mailed Jan. 16, 2007 in corresponding PCT International Application No. PCT/JP006/320781.
"Notification of Transmittal of translation of the IPRP . . . and accompanying forms"for PCT/JP2006/320781, mailed Jun. 19, 2008, 6 pages.

* cited by examiner

*Primary Examiner* — Theodore Stigell
*Assistant Examiner* — Diva K Chander
(74) *Attorney, Agent, or Firm* — Ostrolenk Faber LLP (57) ABSTRACT

At least an inner tube and an outer tube of a double tube, which forms an insertion section of an endoscopic injector, are formed of different kinds of plastic materials, and the outer tube is formed of a material with a higher rigidity than a material of the inner tube. Thereby, there are provided an endoscopic therapeutic device such as an endoscopic injector, and a double tube for a therapeutic device, which have a good operability of, for example, an operation of projecting a needle, and can perform a stable operation for a diseased part.

3 Claims, 6 Drawing Sheets

ENDOSCOPIC THERAPEUTIC DEVICE AND DOUBLE TUBE FOR THERAPEUTIC DEVICE

CROSS REFERENCE TO RELATED APPLICATIONS

This is a Continuation Application of PCT Application No. PCT/JP2006/320781, filed Oct. 18, 2006, which was published under PCT Article 21(2) in Japanese.

This application is based upon and claims the benefit of priority from prior Japanese Patent Application No. 2005-303202, filed Oct. 18, 2005, the entire contents of which are incorporated herein by reference.

BACKGROUND OF THE INVENTION

1. Field of the Invention

The present invention relates to an endoscopic therapeutic device, such as an endoscopic injector, which is introduced into a body cavity through a channel of an endoscope and injects a medicine into a tissue part in the body cavity, and to a double tube for the therapeutic device.

2. Description of the Related Art

In general, a therapeutic device is introduced into a body cavity through a channel of an endoscope, and a diseased part in the body cavity, for instance, is subjected to various medical treatments. Jpn. Pat. Appln. KOKAI Publication No. 2001-58006 (patent document 1) discloses an injector, as an example of an endoscopic therapeutic device, which injects a liquid medicine into, for instance, a diseased part in the body cavity.

The endoscopic injector is provided with an elongated insertion section which is to be inserted into the channel of the endoscope, and an operation section which is coupled to a proximal end portion of the insertion section. The insertion section includes a double tube which comprises an outer tube and an inner tube that is advancibly/retreatably inserted in the outer tube. The operation section performs an advancing/retreating operation of the inner and outer tubes. A hollow needle body is attached to a distal end portion of the inner tube.

When the endoscopic injector is used, the insertion section of the endoscopic injector is introduced into the body cavity through the channel of the endoscope. Then, the inner tube is advanced/retreated, relative to the outer tube, by the operation of the operation section. Thereby, the needle body at the distal end of the inner tube is projected from the distal end portion of the outer tube, or is retreated. At this time, by pushing the inner tube, the needle body is projected from the distal end of the outer tube, thereby puncturing a tissue part in the body cavity.

Conventionally, PTFE or nylon, which has a low surface frictional resistance, is generally used as a material of the outer tube and inner tube. The above-mentioned patent document 1 discloses the use of a fluororesin tube or a nylon tube.

BRIEF SUMMARY OF THE INVENTION

According to a first aspect of the present invention, an endoscopic therapeutic device comprising: an insertion section which is inserted in a channel of an endoscope, the insertion section including a double tube having an outer tube and an inner tube which is advancibly/retreatably inserted in the outer tube; and an operation section which is coupled to a proximal end portion of the insertion section and performs an advancing/retreating operation of the inner and outer tubes, wherein the double tube is configured such that at least the inner tube and the outer tube are formed of different kinds of plastic materials, and the outer tube is formed of a material with a higher rigidity than a material of the inner tube.

In the above-described structure, at least the inner tube and the outer tube are formed of different kinds of plastic materials, and the outer tube is formed of a material with a higher rigidity than a material of the inner tube. Thereby, the magnitude of the resistance of the advancing/retreating operation of the inner and outer tubes can be reduced when the operation section of the endoscopic therapeutic device is operated in the state in which the insertion section is bent, thereby to advance/retreat the inner and outer tubes. In this case, the sliding resistance at the time when the inner and outer tubes are advanced/retreated in the bent state occurs because the outer tube is collapsed and pushed on the inner tube when the inner and outer tubes are bent. Further, in the case where the inner tube has a higher rigidity than the outer tube, the frictional resistance increases due to the phenomenon that the inner tube is strongly rubbed on the inner side of the outer tube which is bent at the time of the operation of projecting the needle by advancing the inner tube relative to the outer tube. In addition, the frictional resistance is greatly influenced by the characteristics of the surfaces that are put in sliding contact. In the case where the material of the inner tube is the same as the material of the outer tube, the outer peripheral surface of the inner tube and the inner peripheral surface of the outer tube, which are put in sliding contact with each other, have mutually close atomic bond states, and these surfaces have high affinity. As a result, the frictional resistance increases. Hence, the hardness of the inner tube is set to be lower than that of the outer tube of the double tube, and the materials of at least the sliding surfaces of the outer tube and inner tube are made different. Thereby, the sliding frictional resistance at the time of advancing/retreating the inner and outer tubes in the state in which the inner and outer tubes are bent can be reduced.

Preferably, the outer tube has a higher bending elasticity modulus than the inner tube.

In the above structure, the outer tube has a higher bending elasticity modulus than the inner tube. Thereby, the sliding frictional resistance at the time of advancing/retreating the inner and outer tubes in the state in which the inner and outer tubes are bent can be reduced.

Preferably, the plastic materials are different kinds of polyolefin plastics, of which the outer tube and the inner tube are formed, respectively.

In the above structure, the outer tube and the inner tube are formed of different kinds of polyolefin plastics. Thereby, the sliding frictional resistance at the time of advancing/retreating the inner and outer tubes in the state in which the inner and outer tubes are bent can be reduced.

Preferably, the plastic materials are a polyolefin plastic and a fluoroplastic, of which the outer tube and the inner tube are formed, respectively.

Preferably, the outer tube is formed of polypropylene and the inner tube is formed of polyethylene.

In the above structure, the outer tube is formed of polypropylene and the inner tube is formed of polyethylene. Thereby, the sliding frictional resistance at the time of advancing/retreating the inner and outer tubes in the state in which the inner and outer tubes are bent can be reduced.

Preferably, the outer tube is formed of polypropylene and the inner tube is formed of PFA.

Preferably, a hollow needle body is attached to a distal end of the inner tube, and the operation section includes a needle body operation section which projects the needle body at the distal end of the inner tube to an outside from a distal end portion of the outer tube, and which retreats the needle body.

In the above structure, the hollow needle body at the distal end of the inner tube is projected to an outside from the distal end portion of the outer tube, and is retreated, by the needle body operation section of the operation section.

Preferably, each of a linear thermal expansion coefficient of the outer tube and a linear thermal expansion coefficient of the inner tube is $20 \times 10^{-5}/°$ C. or less, and a difference between the respective linear thermal expansion coefficients is $5 \times 10^{-5}/°$ C. or less.

According to another aspect of the present invention, a double tube for a therapeutic device, which includes an outer tube and an inner tube which is advancibly/retreatably inserted in the outer tube, wherein the double tube is configured such that at least the inner tube and the outer tube are formed of different kinds of plastic materials, and the outer tube is formed of a material with a higher rigidity than a material of the inner tube.

In the above-described structure, at least the inner tube and the outer tube of the double tube for the therapeutic device are formed of different kinds of plastic materials, and the outer tube is formed of a material with a higher rigidity than a material of the inner tube. Thereby, the magnitude of the resistance of the advancing/retreating operation of the inner and outer tubes can be reduced when the operation section of the endoscopic therapeutic device is operated in the state in which the insertion section is bent, thereby to advance/retreat the inner and outer tubes. In this case, the sliding resistance at the time when the inner and outer tubes are advanced/retreated in the bent state occurs because the outer tube is collapsed and pushed on the inner tube when the inner and outer tubes are bent. Further, in the case where the inner tube has a higher rigidity than the outer tube, the frictional resistance increases due to the phenomenon that the inner tube is strongly rubbed on the inner side of the outer tube which is bent at the time of the operation of projecting the needle by advancing the inner tube relative to the outer tube. In addition, the frictional resistance is greatly influenced by the characteristics of the surfaces that are put in sliding contact. In the case where the material of the inner tube is the same as the material of the outer tube, the outer peripheral surface of the inner tube and the inner peripheral surface of the outer tube, which are put in sliding contact with each other, have mutually close atomic bond states, and these surfaces have high affinity. As a result, the frictional resistance increases. Hence, the hardness of the inner tube is set to be lower than that of the outer tube of the double tube, and the materials of at least the sliding surfaces of the outer tube and inner tube are made different. Thereby, the sliding frictional resistance at the time of advancing/retreating the inner and outer tubes in the state in which the inner and outer tubes are bent can be reduced.

Preferably, the outer tube has a higher bending elasticity modulus than the inner tube.

In the above structure, the outer tube of the double tube for the therapeutic device has a higher bending elasticity modulus than the inner tube. Thereby, the sliding frictional resistance at the time of advancing/retreating the inner and outer tubes in the state in which the inner and outer tubes are bent can be reduced.

Preferably, the plastic materials are different kinds of polyolefin plastics, of which the outer tube and the inner tube are formed, respectively.

In the above structure, the outer tube and the inner tube of the double tube for the therapeutic device are formed of different kinds of polyolefin plastics. Thereby, the sliding frictional resistance at the time of advancing/retreating the inner and outer tubes in the state in which the inner and outer tubes are bent can be reduced.

Preferably, the plastic materials are a polyolefin plastic and a fluoroplastic, of which the outer tube and the inner tube are formed, respectively.

Preferably, the outer tube is formed of polypropylene and the inner tube is formed of polyethylene.

In the above structure, the outer tube of the double tube for the therapeutic device is formed of polypropylene and the inner tube is formed of polyethylene. Thereby, the sliding frictional resistance at the time of advancing/retreating the inner and outer tubes in the state in which the inner and outer tubes are bent can be reduced.

Preferably, the outer tube is formed of polypropylene and the inner tube is formed of PFA.

DETAILED DESCRIPTION OF THE INVENTION

Figure 1A:
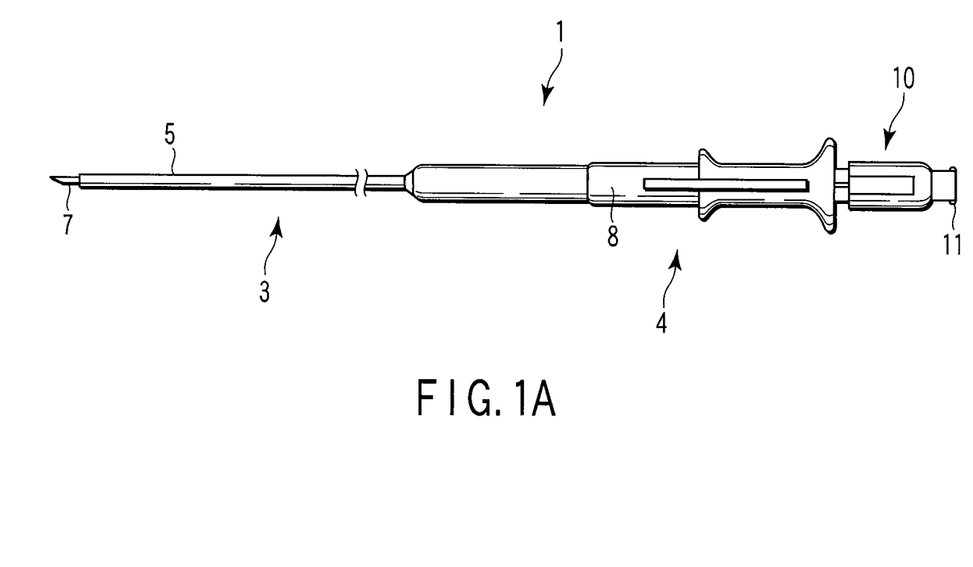
FIG. 1A is a side view showing a state in which a needle is projected from a distal end of an outer tube of an endoscopic injector according to a first embodiment of the present invention.
Figure 1B:
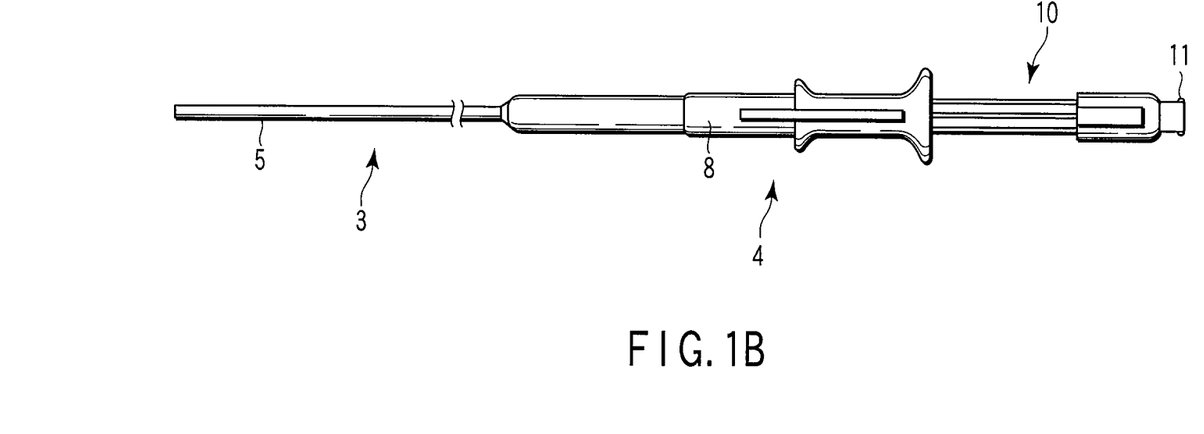
FIG. 1B is a side view showing a state in which the needle is retreated in the outer tube of the endoscopic injector according to the first embodiment.

A first embodiment of the present invention will now be described with reference to the accompanying drawings. FIG. 1A and FIG. 1B show an endoscopic injector 1 according to the present embodiment. The endoscopic injector 1 includes an elongated insertion section 3 which is inserted in a channel of an endoscope 2 (see FIG. 3) and is inserted into the body through the channel, and an operation section 4 which is coupled to a proximal end portion of the insertion section 3.

Figure 2A:
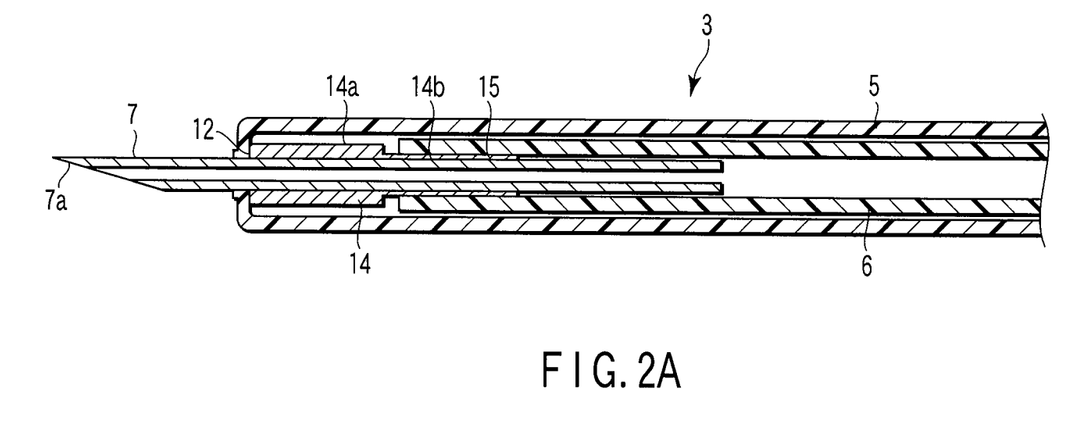
FIG. 2A is a longitudinal cross-sectional view of a main part, showing a state in which the needle is projected from the distal end of the outer tube of the endoscopic injector according to the first embodiment.
Figure 2B:
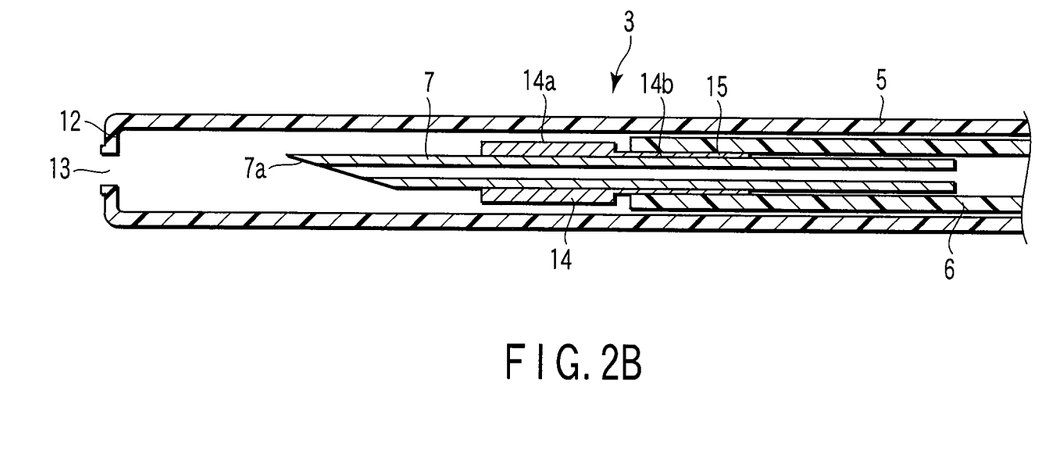
FIG. 2B is a longitudinal cross-sectional view of a main part, showing a state in which the needle is retreated in the outer tube of the endoscopic injector according to the first embodiment.

As shown in FIG. 2A and FIG. 2B, the insertion section 3 includes a double tube which comprises an outer tube 5 and an inner tube 6 that is advancible/retreatable in the outer tube 5. Further, a pipe-shaped needle body 7 is attached to a distal end of the inner tube 6. A pointed puncture portion 7a, which is obliquely cut at an angle of, e.g. 30°, is formed at a needle tip of the needle body 7.

At least the inner tube 6 and outer tube 5 are formed of different kinds of plastic materials, and the outer tube 5 is formed of a material with a higher rigidity than a material of the inner tube 6. In the present embodiment, it is preferable that the outer tube 5 be formed of a plastic material with a higher bending elasticity modulus than a material of the inner tube 6. Further, it is preferable that the outer tube 5 and inner tube 6 be formed of different polyolefin plastics. For example, it is preferable that the outer tube 5 be formed of polypropylene (PP), and the inner tube 6 be formed of low-density polyethylene (LDPE).

Furthermore, in the present embodiment, the outer tube 5 has an inside diameter of ϕ1.8 mm and an outside diameter of ϕ2.3 mm. The inner tube 6 has an inside diameter of ϕ0.7 mm and an outside diameter of ϕ1.5 mm. The needle body 7 is formed of stainless steel material (SUS304).

Figure 2C:
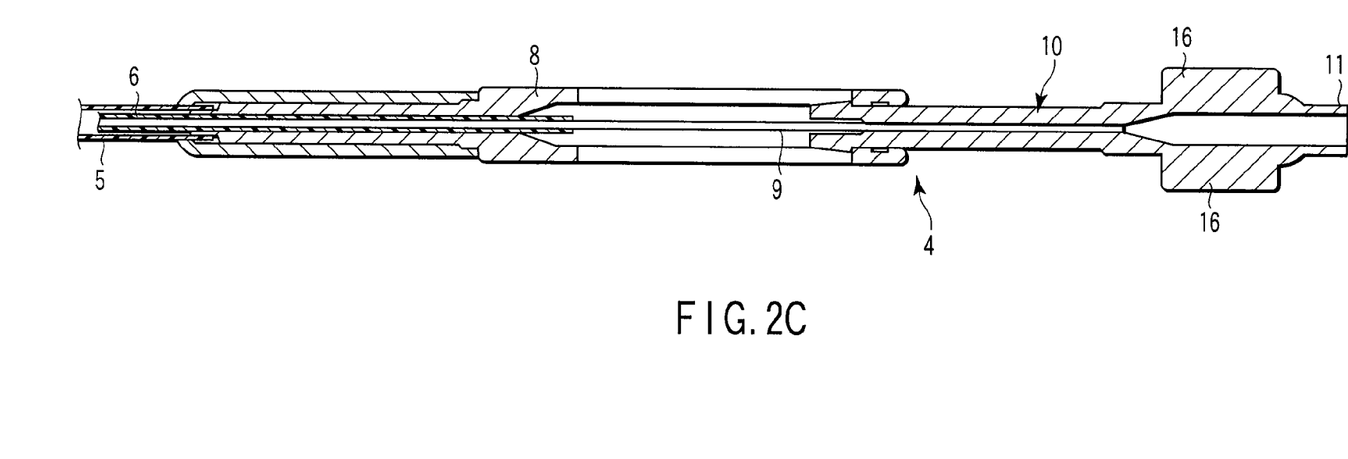
FIG. 2C is a longitudinal cross-sectional view of a main part, showing a state of an operation section in a case where the needle is retreated in the outer tube of the endoscopic injector according to the first embodiment.

The operation section 4 is composed of an operation section body 8 which is fixed to a proximal end portion of the outer tube 5, and a mouthpiece unit 10 which is attached to a proximal end of the inner tube 6 via a stainless-steel pipe 9. As shown in FIG. 2C, the stainless-steel pipe 9 is fixed to a distal end portion of the mouthpiece unit 10 by insert molding. A mouthpiece 11 is formed at a proximal end of the mouthpiece unit 10.

Further, in the operation section 4, the operation section body 8 and mouthpiece unit 10 are advancible/retreatable. As shown in FIG. 1A, if the mouthpiece unit 10 is pushed relative to the operation section body 8, the needle body 7 projects from a distal end opening 13 of the outer tube 5, as shown in FIG. 2A. If the mouthpiece unit 10 is pulled to the proximal side, relative to the operation section body 8, as shown in FIG. 1B and FIG. 2C, the needle body 7 is accommodated in the outer tube 5, as shown in FIG. 2B.

At a distal end portion of the outer tube 5, an engaging abutment portion 12, which is formed of an edge portion projecting radially inward of the outer tube 5, is formed integral with the outer tube 5 in a collar shape by thermal molding. Since the engaging abutment portion 12 is formed in a collar shape, the distal end opening 13 of the outer tube 5, which is formed at the center of the engaging abutment portion 12, is smaller than the inside diameter of the outer tube 5, and the distal end opening 13 is larger than the outside diameter of the needle body 7.

A stepped cylindrical engaging member 14 having a large-diameter portion 14a and a small-diameter portion 14b is fixed on the outer periphery of the needle body 7 by means of so-called caulking (caulking by tightening in plural (2 to 4) directions).

In this case, the outside diameter of the large-diameter portion 14a is less than the inside diameter of the outer tube 5 and is greater than the diameter of the distal end opening 13. Thereby, restriction means is constituted. When the inner tube 6 is pushed relative to the outer tube 5 in the operation of pushing the mouthpiece unit 10 into the operation section body 8 by the operation section 4 and the distal end portion of the needle body 7 is projected from the distal end opening 13 of the outer tube 5, the distal end face of the engaging member 14 abuts on the inner end face of the engaging abutment portion 12 of the outer tube 5. Thus, further advancement is restricted by the restriction means.

The inside diameter of the small-diameter portion 14b of the engaging member 14 is substantially equal to the inside diameter of the inner tube 6. A distal end portion of the inner tube 6 is tightly fitted on the outer periphery of the small-diameter portion 14b. This fitting coupling part is fixed by an adhesive 15. The engaging member 14 is a member which fills a clearance between the outside diameter (outer periphery) of the needle body 7 and the inside diameter (inner periphery) of the inner tube 6. The inner tube 6 and the needle body 7 are coupled via the engaging member 14.

The adhesive 15 is coated so as to also cover a part of the outer peripheral surface of the needle body 7, beyond the proximal end face of the engaging member 14. Thereby, the inner tube 6 and engaging member 14 are bonded and at the same time water-tightness between the needle body 7 and engaging member 14 is ensured.

Figure 3:
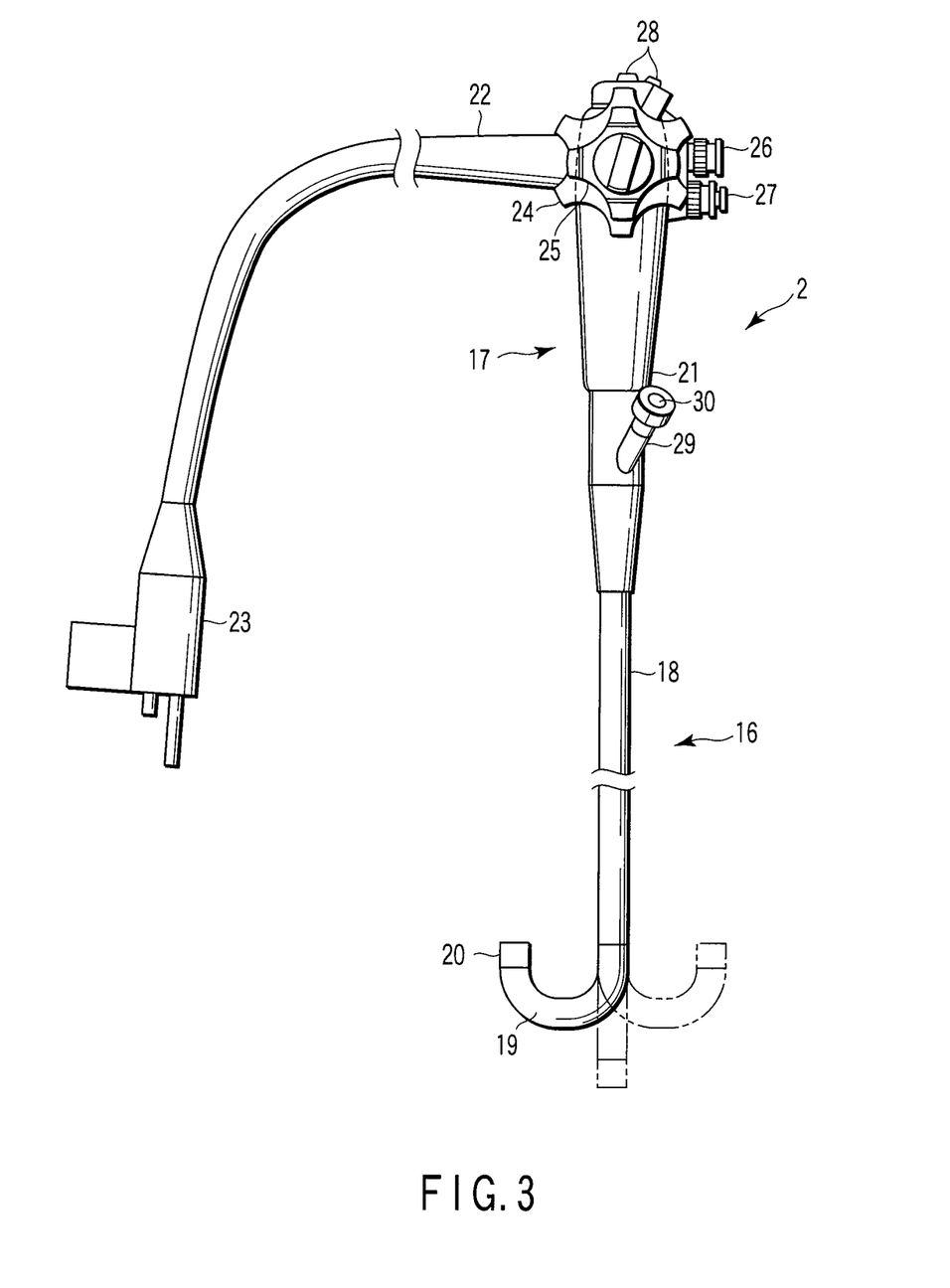
FIG. 3 is a side view showing an example of an endoscope in which the endoscopic injector according to the first embodiment is inserted.

FIG. 3 shows an example of an endoscope 2 in which the endoscopic injector 1 according to the first embodiment is inserted. The endoscope 2 includes an elongated insertion section 16 which is inserted into the body, and an operation section 17 which is coupled to a proximal end portion of the insertion section 16. The insertion section 16 includes an elongated flexible tube section 18, a bending section 19 having a proximal end portion coupled to the distal end of the flexible tube section 18, and a distal-end rigid section 20 having a proximal end portion coupled to the distal end of the bending section 19. A distal end face of the distal-end rigid section 20 is provided with an illumination optical system, an observation optical system, a distal end opening portion of a therapeutic device insertion channel and an air-feed/water-feed nozzle, which are all not shown. The bending section 19 is configured to be bendable from a normal straight state as indicated by a dot-and-dash line in FIG. 3 to a bent state as indicated by a solid line or a two-dot-and-dash line in FIG. 3.

The operation section 17 is coupled to a proximal end portion of the flexible tube section 18. The operation section 17 is provided with a grasping section 21 which is grasped by a surgeon. A proximal end portion of a universal cord 22 is coupled to the grasping section 21. A connector section 23, which is connected to a light source device, a video processor, etc., which are not shown, is coupled to a distal end portion of the universal cord 22.

Further, the grasping section 21 is provided with an up-and-down bending operation knob 24 and a right-and-left bending operation knob 25 for bend-operating the bending section 19, a suction button 26, an air-feed/water-feed button 27, various switches 28 for endoscopic photography, and a therapeutic device insertion section 29. The therapeutic device insertion section 29 is provided with a therapeutic device insertion hole 30 communicating with a proximal end portion of the therapeutic device insertion channel that is provided in the insertion section 16.

The insertion section 3 of the endoscopic injector 1 is inserted into the therapeutic device insertion channel from the therapeutic device insertion hole 30 of the endoscope 2, and is pushed to the distal-end rigid section 20, and then the insertion section 3 is projected outward from the distal end opening portion of the therapeutic device insertion channel.

When the endoscopic injector 1 of the present embodiment is used, the mouthpiece unit 10 is pulled to the movement limit position on the proximal side, relative to the operation section body 8, and the needle body 7 is set in the state in which the needle body 7 is accommodated in the outer tube 5 (the state shown in FIGS. 1B, 2B and 2C. In this state, the insertion section 3 of the endoscopic injector 1 is inserted in the therapeutic device insertion channel of the endoscope 2 that is inserted in the body cavity in advance. Then, the distal end portion of the outer tube 5 of the insertion section 3 is projected into the body cavity from the distal end of the endoscope.

Subsequently, the mouthpiece unit 10 is pushed relative to the operation section body 8, and the needle body 7 is fixed in the state in which the needle body 7 projects from the distal end of the outer tube 5 (the state shown in FIG. 1A and FIG. 2A). In this projecting state, the mouthpiece unit 10 is pushed in by holding the operation section body 8 at the proximal part of the outer tube 5 of the endoscopic injector 1, which is out of the proximal end portion of the therapeutic device insertion channel of the endoscope 2. Thereby, the needle body 7 is made to pierce a target tissue, and a medicine, for instance, is fed by a syringe, which is attached to the mouthpiece 11 in advance, and is injected into the tissue to perform medical treatment.

Next, the operation of the above-described structure is described. When the endoscopic injector 1 of the present embodiment is used, the insertion section 3 of the endoscopic injector 1 is inserted into the body through the therapeutic device insertion channel of the endoscope 2. At this time, the endoscopic injector 1 is operated in the state in which the insertion section 3 of the endoscopic injector 1 is bent in accordance with the shape of the insertion section 16 of the endoscope 2. The sliding resistance at the time when the inner tube 6 and outer tube 5 are advanced/retreated in the bent state occurs because the outer tube 5 is collapsed and pushed on the inner tube 6 when the inner tube 6 and outer tube 5 are bent. Further, in the case where the inner tube 6 has a higher rigidity than the outer tube 5, the frictional resistance increases due to the phenomenon that the inner tube 6 is strongly rubbed on the inner side of the outer tube 5 which is bent at the time of the operation of projecting the needle body 7 by advancing the inner tube 6 relative to the outer tube 5.

In addition, in the case where the material of the inner tube 6 is the same as the material of the outer tube 5, the outer peripheral surface of the inner tube 6 and the inner peripheral surface of the outer tube 5, which are put in sliding contact with each other, have mutually close atomic bond states, and these surfaces have high affinity. As a result, the frictional resistance increases. Besides, the frictional resistance is greatly influenced by the characteristics of the surfaces that are put in sliding contact. Hence, as regards the hardness of the double tube of the insertion section 3 of the endoscopic injector 1, the hardness of the inner tube 6 is set to be lower than that of the outer tube 5, and the materials of at least the sliding surfaces of the outer tube 5 and inner tube 6 are made different. Thereby, the frictional resistance at the time of bending can be decreased. The hardness of the outer tube 5 and inner tube 6, which has been described above, greatly affects the frictional resistance at the time of bending of the double tube comprising the outer tube 5 and inner tube 6, and thus a bending elasticity modulus may be substituted for the characteristic of the material.

The measurement of the operation force amount of the double tube for the therapeutic device, which is assembled in the insertion section 3 of the endoscopic injector 1 according to the present embodiment, was conducted as follows. When the operation force amount of the double tube is measured, the inner tube 6 is advanced/retreated in the outer tube 5 in the state in which the insertion section 3 of the endoscopic injector 1 is inserted in the therapeutic device insertion channel of the endoscope 2. In this case, the endoscope 2 is held in a bent state in which the flexible tube section 18 of the insertion section 16 is wound by a single loop with a proper diameter (e.g. a radius R of 50 mm).

Then, the insertion section 3 of the endoscopic injector 1 is inserted in the therapeutic device insertion channel from the therapeutic device insertion hole 30 of the endoscope 2 and is operated and pushed to the distal-end rigid section 20, and the insertion section 3 is set in the state in which the insertion section 3 projects from the distal end opening of the therapeutic device insertion channel. In this state, the work for measuring the operation force amount of the double tube for the therapeutic device of the insertion section 3 of the endoscopic injector 1 is conducted. Thereby, in the state in which the insertion section 3 of the endoscopic injector 1 is bent and wound by a single loop along the shape of the therapeutic device insertion channel of the endoscope 2, the force amount of sliding is measured with the amount of projection of the needle body 7 being set at, e.g. 30 mm.

Table 1 shows a measurement result of the operation force amount (N) of the double tube for the therapeutic device of the insertion section 3 of the endoscopic injector 1 in the case where the combination of the plastic material of the inner tube 6 and the plastic material of the outer tube 5 of the double tube for the therapeutic device of the insertion section 3 of the endoscopic injector 1 is varied.

TABLE 1

| No. of experiment | Outer tube | Inner tube | Operation force amount (N) |
|---|---|---|---|
| 1 | PP | PP | 7.15 |
| 2 | HDPE | HDPE | 10 or more |
| 3 | PTFE | PTFE | 5.62 |
| 4 | HDPE | PP | 4.94 |
| 5 | PP | LDPE | 0.25 |
| 6 | PP | LLDPE | 0.80 |
| 7 | PP | PFA | 0.24 |

The data of the double tube for the therapeutic device, which was used in the measurement experiment of the operation force amount (N) of the double tube for the therapeutic device, is as follows:

Inner tube 6: the outside diameter is 1.5 mm and the inside diameter is $\phi$0.7 mm.

Outer tube 5: the outside diameter is $\phi$2.3 mm and the inside diameter is $\phi$1.8 mm.

Table 2 shows the characteristics of the materials which were used in the measurement of the operation force amount (N) of the double tube for the therapeutic device.

TABLE 2

| Material | Bending elasticity modulus | Hardness |
|---|---|---|
| PP | 1500 MPa | R100 |
| PTFE | 550 MPa | D55 |
| HDPE | 1050 MPa | D67 |
| LDPE | 130 MPa | D49 |
| LLDPE | 330 MPa | D53 |

In Table 2, R is Rockwell hardness, and D is Shore hardness. Of the materials, HDPE is a high-density polyethylene, and LLDPE is linear low-density polyethylene. It is preferable that any of the materials in Table 2 be transparent or semi-transparent, so that the presence/absence of bubbles and the condition of passage of liquid medicine can be confirmed when liquid medicine, or the like, is passed through the double tube.

As indicated in the measurement experiment result in Table 2 of the operation force amount (N) of the double tube for the therapeutic device, in the case where the outer tube 5 and inner tube 6 are formed of the same material as in the cases of experiment Nos. 1 to 3, the operation force amount (N) is relatively high, namely, 7.15, 10 or more, and 5.62. In the case where the hardness of the outer tube 5 is lower than that of the inner tube 6, as in the case of experiment No. 4, the operation force amount (N) is 4.94 and is also high.

By contrast, in the case where the present invention is applied (i.e. the hardness of the inner tube 6 is lower than that of the outer tube 5) as in the cases of experiment Nos. 5 and 6, the operation force amount (N) is relatively low, namely, 0.25 and 0.80. It is thus confirmed that the operation force amount is smaller in the case where the hardness of the inner tube 6 is lower than that of the outer tube 5 (experiment Nos. 5 and 6)

than in the case where the inner tube 6 and outer tube 5 are formed of the same material (experiment Nos. 1 to 3) or in the case where the hardness of the outer tube 5 is lower than that of the inner tube 6 (experiment No. 4).

As is clear from the measurement result of Table 1, the operation force amount (N) can be decreased in the case where the hardness of the inner tube 6 is lower than that of the outer tube 5. As regards the combination of the outer tube 5 of PP and the inner tube 6 of LLDPE as in the case of experiment No. 6, in the case where the thickness of the inner tube 6 was reduced such that the outside diameter was set at 1.5 mm and the inside diameter was set at φ0.9 mm, the operation force amount (N) decreased to 0.55.

The following advantageous effects are obtained with the above-described structure. Specifically, in the endoscopic injector 1 according to the present embodiment, at least the inner tube 6 and outer tube 5 are formed of different kinds of plastic materials, and the outer tube 5 is formed of a material with a higher rigidity than a material of the inner tube 6. Thus, when the operation section 4 is operated and the operation of projecting the needle body 7 is performed by advancing the inner tube 6 relative to the outer tube 5 in the state in which the insertion section 3 of the endoscopic injector 1 is bent, the magnitude of the sliding frictional resistance between the inner tube 6 and the outer tube 5 can be reduced. Therefore, even in the case where medical treatment by the endoscopic injector 1 is performed in the state in which the insertion section 3 that is inserted in the body is bent, the operability of the operation of projecting the needle body 7 of the endoscopic injector 1 from the distal end opening 13 of the outer tube 5 is good, and a stable operation can be performed for a diseased part.

In addition, as in the case of experiment No. 7, even if the material of the inner tube 6 is replaced with PFA, the operation force amount that is substantially equal to the case of using LDPE is indicated. Thus, the same effect can be obtained even in the case of using fluoroplastics.

In the endoscopic injector 1 using the double tube comprising the inner tube 6 and outer tube 5, if the hardness and material are varied, the linear thermal expansion coefficient varies accordingly. Thus, such a phenomenon may possibly occur that the needle body 7 projects from the distal end opening 13 of the outer tube 5 due to thermal variation (thermal expansion) even at times when there is no need. In addition, when the needle body 7 projects from the distal end opening 13 of the outer tube 5 at a time when necessary, the needle body 7 may not smoothly project.

Normally, the temperature of the environment of use of the endoscopic injector 1 is about 36° C. since the endoscopic injector 1 is used in the body. On the other hand, the temperature of the environment of the therapeutic treatment room is, in general, about 25 to 28° C. Thus, the difference between the temperature of the environment of the therapeutic treatment room and the temperature of the environment of use in the body is about 10° C. In the present embodiment, the linear thermal expansion coefficient is so set as to prevent occurrence of problems in projection/retreat of the needle body 7 due to linear thermal expansion or contraction at these temperatures. Specifically, the difference between the linear thermal expansion coefficient of the material of the inner tube 6 and the linear thermal expansion coefficient of the material of the outer tube 5 is set at $5\times10^{-5}/°$ C. or less. Thereby, it becomes possible to prevent such a phenomenon that the needle body 7 projects from the distal end opening 13 of the outer tube 5 due to thermal variation (thermal expansion), or such a phenomenon that the projection of the needle body 7 becomes unsmooth when the needle body 7 is projected, where necessary, from the distal end opening 13 of the outer tube 5.

Furthermore, if the length of the therapeutic device insertion channel of the endoscope 2 is large, if there is a difference between the linear thermal expansion coefficient of the material of the inner tube 6 and the linear thermal expansion coefficient of the material of the outer tube 5, there is a possibility that necessary treatment cannot be performed, for example, because the needle body 7 may not reach a diseased part when the needle body 7 is projected from the distal end opening 13 of the outer tube 5. It is thus preferable that the linear thermal expansion coefficient of the material of each of the inner tube 6 and outer tube 5 be set at $20\times10^{-5}/°$ C. or less.

The present invention is not limited to the above-described embodiment and, needless to say, the invention may variously be modified in practice without departing from the spirit of the invention.

The present invention is effective in a technical field of using an endoscopic therapeutic device such as an endoscopic injector, and a double tube for a therapeutic device, and in a technical field of manufacturing the endoscopic therapeutic device such as an endoscopic injector, and the double tube for a therapeutic device.

What is claimed is:

1. An endoscopic therapeutic device comprising:
    a double tube configured to be inserted through a channel of an endoscope, wherein the double tube includes:
    a flexible outer tube; and
    a flexible inner tube inserted through the outer tube and configured to be advanced and retracted relative to the outer tube,
    wherein in the double tube,
    the inner tube and the outer tube are made of different types of plastic materials such that an affinity between an outer circumferential sliding contact surface of the inner tube, and an inner circumferential sliding contact surface of the outer tube is reduced, as compared to where the inner tube and outer tube are made of a same type of plastic material, and a frictional resistance between the sliding contact surfaces is lowered when the inner tube and the outer tube are relatively advanced or retracted while the double tube is curved to follow a pathway of the channel, and
    the outer tube is made of a material more rigid than that of the inner tube such that crushing of the outer tube at a bent position of the double tube which follows the pathway of the channel is prevented and an increase in the frictional resistance between the sliding contact surfaces when the inner tube and the outer tube are relatively advanced or retracted is prevented.

2. The endoscopic therapeutic device according to claim 1, wherein the inner tube is made of one of LDPE, LLDPE and PFA, and the outer tube is made of polypropylene.

3. The endoscopic therapeutic device according to claim 1, wherein
    a material of the inner tube has a bending elasticity modulus within a range of substantially 8% to 45% of a bending elasticity modulus of a material of the outer tube.

* * * * *